US010745330B2

(12) United States Patent
Ramasamy et al.

(10) Patent No.: US 10,745,330 B2
(45) Date of Patent: Aug. 18, 2020

(54) METHOD OF CONVERTING ETHANOL TO HIGHER ALCOHOLS

(71) Applicant: BATTELLE MEMORIAL INSTITUTE, Richland, WA (US)

(72) Inventors: Karthikeyan K. Ramasamy, West Richland, WA (US); Mond F. Guo, Richland, WA (US); Michel J. Gray, Kennewick, WA (US); Senthil Subramaniam, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 16/046,395

(22) Filed: Jul. 26, 2018

(65) Prior Publication Data

US 2019/0031585 A1 Jan. 31, 2019

Related U.S. Application Data

(60) Provisional application No. 62/537,656, filed on Jul. 27, 2017.

(51) Int. Cl.
C07C 29/34 (2006.01)
C07C 29/32 (2006.01)

(52) U.S. Cl.
CPC .............. C07C 29/34 (2013.01); C07C 29/32 (2013.01)

(58) Field of Classification Search
CPC ................................ C07C 29/34; C07C 29/32
See application file for complete search history.

(56) References Cited

U.S. PATENT DOCUMENTS

| 1,992,480 | A | 2/1935 | Fuchs et al. | |
| 9,018,427 | B2* | 4/2015 | Gadewar | B01J 23/00 568/881 |
| 2013/0172634 | A1 | 7/2013 | Yoshioka et al. | |
| 2014/0088326 | A1 | 3/2014 | Norman et al. | |
| 2014/0171696 | A1* | 6/2014 | Zhang | C07C 29/34 568/905 |
| 2014/0235901 | A1 | 8/2014 | Gadewar et al. | |

OTHER PUBLICATIONS

Angelici, C., et al., Effect of Preparation Method and CuO Promotion in the Conversion of Ethanol into 1,3-Butadiene over SiO2—MgO Catalysts, ChemSusChem, 7, 2014, 2505-2515.
Carotenuto, G., et al., Kinetic study of ethanol dehydrogenation to ethyl acetate promoted by a copper/copper-chromite based catalyst, Catalysis Today, 203, 2013, 202-210.
Cassinelli, W. H., et al., Time-resolved XAS/MS/Raman monitoring of mutual copper sefl-reduction and ethanol dehydrogenation reactions, RSC Advances, 6, 2016, 20453-20457.
Dewilde, J. F., et al., Ethanol Dehydration and Dehydrogenation on y-Al2O3: Mechanism of Acetaldehyde Formation, ACS Catalysis, 4, 2014, 4425-4433.
Freitas, I. C., et al., Effect of Cu content on the surface and catalytic properties of Cu/ZrO2 catalysts for ethanol dehydrogenation, Journal of Molecular Catalysis A: Chemical, 381, 2014, 26-37.
Goulas, K. A., et al., Synergistic Effects in Bimetallic Palladium-Copper Catalysts Improve Selectivity in Oxygenate Coupling Reactions, Journal of the American Chemical Society, 138, 2016, 6805-6812.
Hilbrandt, N., et al., An Extended in Sity Cu—K XAFS and XRD Study on the Site Preference and Valence of Copper Ions in (Mg1—xCux)O, Journal of Physical Chemistry B, 103, 1999, 4797-4802.
Inui, K., et al., Effective formation of ethyl acetate from ethanol over Cu—Zn—Zr—Al—O catalyst, Journal of Molecular Catalysis A: Chemical, 216, 2004, 147-156.
Knaeble, W., et al., Kinetic and Theoretical Insights into the Mechanism of Alkanol Dehydration on Solid Bronsted Acid Catalysts, The Journal of Physical Chemistry C, 120, 2016, 3371-3389.
Luggren, P. J., et al., Upgrading of biomass-derived 2-hexanol to liquid transportation fuels on Cu—Mg—Al mixed oxides. Effect of Cu content, Fuel, 177, 2016, 28-38.
Ro, I., et al., Role of the Cu—ZrO2 Interfacial Sites for Conversion of Ethanol to Ethyl Acetate and Synthesis of Methanol from CO2 and H2, ACS Catalysis, 6, 2016, 7040-7050.
Sun, Z., et al., Efficient Catalytic Conversion of Ehtanol to 1-Butanol via the Guerbet Reaction over Copper- and Nickel-Doped Porous, ACS Sustainable Chemistry & Engineering, 5, 2017, 1738-1746.
Torresi, P. A., et al., Upgrading of diols by gas-phase dehydrogenation and dehydration reactions on bifunctional Cu-based oxides, Catalysis Science & Technology, 4, 2014, 3203-3213.
Xu, I., et al., Isobutanol and Methanol Synthesis on Copper Catalysts Supported on Modified Magnesium Oxide, 171, 1997, 130-147.
Notification of Transmittal of the International Search Report and the Written Opinion of the International Searching Authority for International Application No. PCT/US18/44028, International Filing Date Jul. 27, 2018, dated Oct. 11, 2018.
Liu, J., et al., Sintering-Resistant Nanoparticles in Wide-Mouthed Compartments for Sustained Catalytic Performance, Scientific Reports 7 (Feb. 3, 2017), 2017, 1-8.
Pramod, C. V., et al., Coupling of Cyclohexanol Dehydrogenation-nitrobenzene Hydrogenation Over MgO—Al2O3 Hydrotalcite Supported Cu Catalysts: Effect of Cu Loading, Current Catalysis, 1 (Aug. 1, 2012), 140-148.
Liu, J., Catalysis by Supported Single Metal Atoms, ACS Catalysis 7.1 (Nov. 29, 2016), 34-59.
Bravo-Suarez, J. J., et al., Vapor-phase methanol and ethanol coupling reactions on CuMgAl mixed metal oxides, Applied Catalysis A: 455, 2013, 234-246.

(Continued)

Primary Examiner — Rosalynd A Keys
(74) Attorney, Agent, or Firm — Derek H. Maughan

(57) ABSTRACT

A method and catalyst for forming higher alcohols from lower alcohol feedstocks. In one application a highly selective and stable copper pseudo-single-atom supported on MgO—Al₂O₃ catalyst is provided which provides ethanol condensation to higher alcohols at ~50% yields and ~85% selectivity is demonstrated with stable catalyst lifetime over 500 hours in a continuous flow system. In some applications a Guerbet condensation process is further utilized to yield a higher alcohol at a selectivity of near ~90%.

4 Claims, 4 Drawing Sheets

(56) References Cited

Ramasamy, K. K., et al., Tunable catalytic properties of bi-functional mixed oxides in ethanol conversion to high value compounds, Catalysis Today, 2016, 1-6.

Gole, J. L., et al., Nanocatalysis: Selective Conversion of Ethanol to Acetaldehyde Using Mono-atomically Dispersed Copper on Silica Nanospheres, Journal of Catalysis, 204, 2001, 249-252.

* cited by examiner

METHOD OF CONVERTING ETHANOL TO HIGHER ALCOHOLS

PRIORITY

This application claims priority from provisional patent application entitled Conversion of Ethanol to Higher Alcohols filed Jul. 27, 2017 application No. 62/537,656.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

BACKGROUND OF THE INVENTION

Field of the Invention

The invention generally relates to chemical and chemical synthesis and more particularly to systems and methodologies for upgrading and modifying alcohols such as ethanol to form higher alcohols useful in the production in a variety of other products.

Background Information

Ethanol is a commercially produced chemical with domestic production near 15 billion gallons. Despite its broad availability, extensive utilization of ethanol based products has been limited due to a variety of factors. Among these factors is the so called "blend wall" whereby the inclusion of ethanol is limited in its applications based upon concerns in the industry about negative associated complications. This is true for example in gasoline markets where current inclusion is typically limited to around 10%, while other types of higher order fuels do not have these same lower thresholds. What is needed therefore is a way to inexpensively and efficiently upgrade ethanol feedstocks to form higher level products that can be utilized as replacements (in whole or in part) from fossil fuel derived materials. The present disclosure provides examples of developments that meet these needs.

Additional advantages and novel features of the present disclosure will be set forth as follows and will be readily apparent from the descriptions and demonstrations set forth herein. Accordingly, the following descriptions of the present disclosure should be seen as illustrative of the disclosure and not as limiting in any way.

SUMMARY

A method is described for converting an ethanol containing feedstock to a higher level alcohol including the step of introducing the feedstock to a CuO—MgO—Al2O3 catalyst having less than 0.25 wt % Cu under hydrogen at a pressure above 200 psig to facilitate in-line process intensification selectively form a preselected higher alcohol product. In one set of exmples the method is performed at a temperature between 275-350 degrees C. In various variations the catalyst may be a sinter resistant catalyst, may comprise dispersed copper sites at an atomic level on a Mg/Al mixed oxide catalyst. The copper may be $Cu^{+1}$, which may be a stabilized copper pseudo-single-atom supported on MgO—Al2O3 catalyst. Preferably the copper percentage is between 0.1 wt % and 0.25 wt %.

In some instances, additional steps such as condensing the preselected higher alcohol product through a Guerbet reaction to yield a second product, or passing the second product from the Guerbet reaction through a second catalyst bed to improve selectivity to alcohols via conversion of esters and aldehydes and minimize downstream separation may also be incorporated. In one set of experiments this yielded a higher alcohol at a selectivity of over 80% which is very high compared to the other known technologies. In addition the use of very mild conditions (a hydrogen atmosphere at 325 degrees C. and 300 psig) enabled the catalyst life time to extend toward ~250 h without any deactivation towards selectivity of the conversion. Further improvements will reduce the complexity of the process, improve the overall selectivity and yield to the higher alcohols, improve catalyst life time, and reduce material and catalyst synthesis costs.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

DETAILED DESCRIPTION

The following description includes a preferred best mode of one embodiment of the present disclosure. It will be clear from this description of the disclosure that the disclosure is not limited to these illustrated embodiments but that the disclosure also includes a variety of modifications and embodiments thereto. Therefore the present description should be seen as illustrative and not limiting. While the disclosure is susceptible of various modifications and alternative constructions, It should be understood, that there is no intention to limit the disclosure to the specific form disclosed, but, on the contrary, the disclosure is to cover all modifications, alternative constructions, and equivalents falling within the spirit and scope of the disclosure as defined in the claims.

The present application describes a methodology for inexpensively and efficiently upgrading feedstocks such as ethanol to form higher level products that can be utilized in existing applications as replacements (in whole or in part) from fossil fuel derived materials. In one set of experiments, it was shown that alcohol coupling paves the path for the production of the key intermediates for the generation of paints, adhesives and coating from the renewable resources that are otherwise generated from the fossil based resources.

Most of the currently reported multi-functional catalysts for alcohol coupling lack the product selectivity, yields and catalyst stability due to the complex nature of the chemistry and the non-selective interaction with the different functionality of the catalyst. The present application describes a new catalyst and process by utilzing a highly selective and stable copper pseudo-single-atom supported on $MgO-Al_2O_3$ catalyst for alcohol coupling chemistry. The use of this catalyst in the described process coupled with ethanol condensation to higher alcohols at ~50% yields and ~85% selectivity is demonstrated with stable catalyst lifetime over 200 hours in a continuous flow system. The superior performance of the alcohol coupling can be attributed to the absence of Cu—Cu metallic bonding, which favors the formation of ketones and other side products via cross-coupling reaction.

Figure 1:
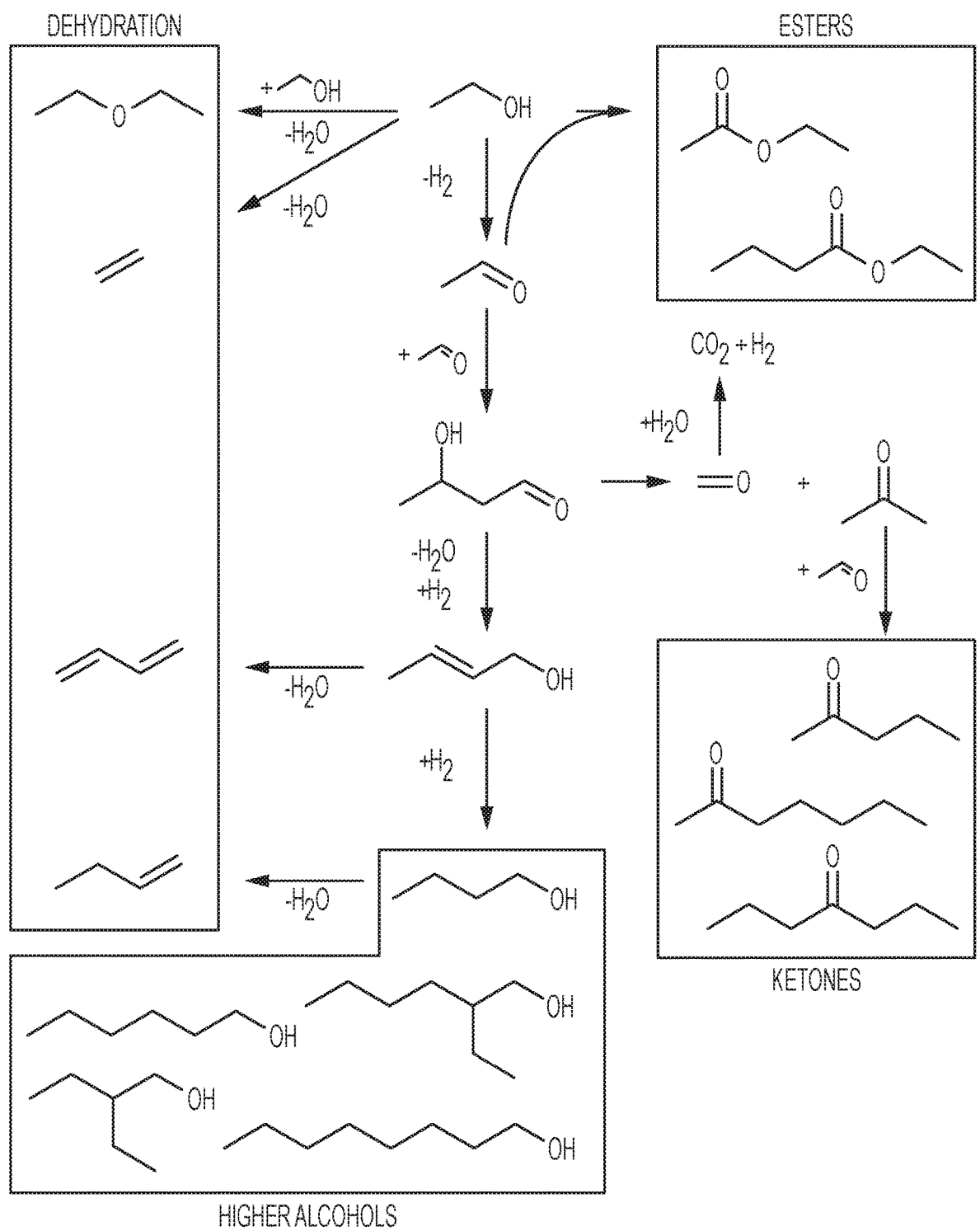
FIG. 1 shows reaction pathways showing ethanol coupling to butanol as well as possible side reactions resulting from dehydration, esterification, and C-C scission to form ketones.

FIG. 1 shows the complexity of the multi-step cascade chemistry and susceptibility to side reactions that has hindered most ethanol conversion to higher alcohols process. Current strategies utilize multi-functional catalysts using tunable supports with the acid/base surface chemistry necessary for aldol condensation, paired with a redox active catalyst to promote the initial dehydrogenation step. One of the fundamental challenges in controlling the reaction after the introduction of redox active materials is the promotion of side reaction(s) due to the imbalance between the different catalytic functionalities on the surface (redox, base and acid), lack of control over size of metal clusters, and morphologies. The present approach overcomes these concerns by developing a single atom (atomically dispersed) sinter resistant catalyst that can selectively target the dehydrogenation of ethanol with high yields to the higher alcohol formation.

As described below, highly dispersed single atom copper sites on layered double hydroxide (LDH) derived Mg/Al mixed oxide catalyst can be achieved using co-precipitation synthesis. In operando X-ray absorption spectroscopy (XAS) and transmission electron microscopy (TEM) study reveal that at sufficiently low concentrations (<0.1 wt %), copper becomes stabilized on the support as an isolated monovalent site, resistant to reduction and sintering even under highly reductive and high temperature operating conditions. The predominant $Cu^{+1}$ species was found to be highly effective at promoting the initial dehydrogenation of ethanol, leading to improved ethanol conversion to higher alcohols. The appearance of $Cu^0$ at higher copper concentrations lead to sintering of metal and coincided with a major shift towards reaction side products.

Preserving the $Cu^{+1}$ species as the primary site and preventing the formation of $Cu^0$ state allowed for unprecedented yields of higher alcohols from ethanol, with stable catalyst performance demonstrated over extended (>500 hours) lifetime runs. This straightforward approach to achieve single atom catalysis and the discovery of $Cu^{+1}$ as a highly selective species opens a novel pathway to overcome many of the longstanding hurdles barring the development of viable catalytic processes for the sustainable production of higher alcohols from renewable ethanol.

In one specific case a CuMgAl hydrotalcite catalyst was synthesized via the co-precipitation of metal salt precursors from a homogenous mixed and titrated solution. $Mg(NO_3)_2.6H_2O$ and $Al(NO_3)_3.6H_2O$ were dissolved in aqueous solution in the desired stoichiometric Mg:Al ratio and pumped into a 60° C. solution of $Na_2CO_3.10H_2O$ that was titrated by 1 M NaOH, using a pH controller to automatically maintain a pH of 11. To introduce the copper promoter, $Cu(NO_3)_2.xH_2O$ was added to the initial precursor solution to obtain a calculated copper loading in weight percent of the final catalyst. Under steady titration and vigorous mixing, a precipitate suspension was formed that was then aged for 20 hours at 60° C. The precipitate was separated by filtration, and washed with 60° C. deionized water until ion concentrations dropped below 50 ppm in the wash effluent. The formed catalyst was dried overnight at 100° C., then pelletized at 16000 psig prior to calcination in air at 600° C. for 2 hours with 4° C./min ramping, and subsequent sizing between 35-100 mesh sieves. Catalysts containing copper were reduced in-situ by 50 mL/min of pure $H_2$ at ambient pressure for 80 minutes at 350° C. prior to all experimental runs, and protected by $N_2$ or $H_2$ carrier gas at all times. All catalyst precursor materials were purchased from Sigma-Aldrich. A set of catalysts were prepared via co-precipitation using a varying molar ratio of Mg and Al (2:1, 3:1, 4:1, 5:1, 6:1) to generate the LDH structure. Copper was added in a range of concentrations from 0.025% to 0.25% calculated by weight percent of the total metal content. X-ray diffraction (XRD) patterns of the uncalcined catalyst verified the formation of the layered hydroxide structure, with no significant differences between different copper concentrations. The actual metal content post-synthesis was measured by inductive coupled plasma (ICP), which determined the final Mg/Al atomic ratio.

TABLE 1

Composition of Catalysts determined by ICP Analysis

| Nominal Cu Content (wt %) | Weight % of Total Metal Content | | | Relative Atomic Ratios | | |
| --- | --- | --- | --- | --- | --- | --- |
| | Cu | Mg | Al | Cu | Mg | Al |
| 0% | — | 77.43 | 22.57 | — | 3.43 | 1 |
| 0.05% | 0.09 | 77.00 | 22.91 | 0.0038 | 3.42 | 1 |
| 0.1% | 0.16 | 77.45 | 22.39 | 0.0072 | 3.46 | 1 |
| 0.25% | 0.39 | 77.77 | 21.83 | 0.0179 | 3.56 | 1 |
| 0* | — | 77.08 | 22.92 | — | 3.36 | 1 |
| 0.05%* | 0.09 | 76.59 | 23.32 | 0.0038 | 3.28 | 1 |
| 0.1%* | 0.16 | 77.16 | 22.57 | 0.0071 | 3.40 | 1 |
| 0.25%* | 0.41 | 77.24 | 22.35 | 0.0183 | 3.46 | 1 |

*Spent catalyst measured after reaction

Various samples of these catalysts were then incorporated into a set of experiments performed in a fixed-bed tubular reactor using a down flow vapor-phase setup under atmospheric and 1500 psig pressure maintained by a back pressure regulator. 2 g of catalyst were packed in the isothermal zone at varying temperature between 275° C. and 350° C. maintained by a tube furnace, and 0.002-0.01 mL/min of ethanol was co-fed with 2-50 mL/min of carrier gas ($N_2$ or $H_2$) across the bed. Product was separated into a gas and liquid phase via cold trap maintained at 4° C.; gas product flow was measured by DryCal and analyzed by a gas chromatography-thermal conductivity detector, while the condensed liquid products were identified via gas chromatography-mass spectroscopy and quantitated by a flame-ionization detector using internal/external standards. Experiments were run for at least three days on stream in order to reach steady state conditions, with regular gas sampling every 4 hours and liquid sampling every 24 hours. All reported data was taken at ~60 hours time-on-stream unless otherwise noted. Mass and carbon balances were calculated to be >95% and all selectivities are given on a carbon basis.

Running the reaction with $H_2$ gas instead of an inert $N_2$ changed the resulting products, for example a significant rise in the dehydration related products, including, specifically the as well as trace amounts of 2-butenol and cyclic compounds such as benzene and xylene was noted. Table 2 shows the results obtained from visual comparison between the catalysts run in the $H_2$ and $N_2$ environment reflects this difference; spent catalyst from the $N_2$ set is covered in brownish carbonaceous material, while the spent catalyst from the $H_2$ runs are a light grey that do not significantly differ in appearance from the reduced catalyst. High $H_2$ partial pressure provides two critical benefits to the reaction. The first is that it promotes the formation of 1-butanol over diethyl ether and other acid dehydration products. The second is that it allows for the rapid hydrogenation of C—C double bonds, converting to stable saturated products such as 1-butanol and 1-hexanol. This in turn reduces the chances of further condensation of the unsaturated reactive aldehyde to generate high molecular weight compounds and block/strongly adsorb on the catalyst active sites. It can be seen that a high partial pressure of $H_2$ increases product selectivity towards higher alcohols, maintaining catalyst stability and preventing deactivation.

selectivity as well as conversion. Ketone and ester side product formation greatly increase when deviating from this ratio. At a ratio of Mg/Al of 2, the selectivities to esters and ketones are similar to that of a $Mg_4Al_1$+0.25% Cu catalyst, with a similar resemblance in the XAS data demonstrating the abundance of metallic copper. This suggests that the Mg/Al ratio plays a critical role in securing the monoatomically disperse character of the catalyst, and that the aggregation of copper is the primary barrier to high selectivity.

TABLE 3

|  | Aldehydes | Ketones | Esters | Alkenes | Ethers | CO2 | Total Alcohols | Higher Alcohols | 1-Butanol | Conversion |
| --- | --- | --- | --- | --- | --- | --- | --- | --- | --- | --- |
| Mg2Al1 + 0.1%Cu | 2.74 | 15.08 | 21.23 | 3.69 | 1.84 | 4.23 | 50.79 | 16.18 | 33.50 | 57.25 |
| Mg3Al1 + 0.1%Cu | 9.40 | 6.22 | 14.36 | 4.13 | 0.95 | 1.76 | 62.64 | 15.74 | 46.90 | 61.75 |
| Mg4Al1 + 0.1%Cu | 9.36 | 3.40 | 8.90 | 2.63 | 1.10 | 1.01 | 73.60 | 23.21 | 50.39 | 68.82 |
| Mg5Al1 + 0.1%Cu | 3.62 | 5.09 | 17.06 | 2.78 | 1.95 | 1.51 | 67.99 | 19.15 | 48.65 | 52.16 |

The method of synthesis has a significant impact on the conversion and selectivity of the product. Catalysts prepared from incipient wetness or impregnation differ in their results and characterization from coprecipitated catalyst, even with the same support makeup and copper loading, particularly at low copper concentrations below 0.25% Cu loading. Results comparing these two synthesis methods are reported in Table 4 for both 0.1% and 0.25% Cu loadings on Mg4A1 support. The coprecipitated catalyst demonstrate a much higher conversion compared to the impregnated catalysts. For 0.25% Cu metal loading, the selectivity to alcohols are similar at around 46%. Between the 0.1% Cu catalysts however, the selectivity to alcohols is much greater for the coprecipitated catalyst, primarily due to the reduction in esters and ketone side products. The impregnated 0.1% Cu catalyst instead yields results similar to that of the 0.25% Cu, with less than 50% selectivity to alcohols with esters being the primary side product. This suggests that the impregnation process much more easily leads to the copper aggregation, leading to a product spectrum with low selectivity. Coprecipitation can yield a catalyst with a much higher dispersion of copper and

TABLE 2

|  | Gas | Aldehydes | Ketones | Esters | HCs | Ethers | CO2 | Total Alcohols | Higher Alcohols | 1-Butanol | Conversion |
| --- | --- | --- | --- | --- | --- | --- | --- | --- | --- | --- | --- |
| Mg4Al1 + 0.1%Cu | N2 | 3.28 | 0.89 | 3.06 | 9.80 | 18.02 | 0.43 | 64.05 | 7.79 | 56.12 | 38.78 |
| Mg4Al1 + 0.1%Cu | H2 | 9.36 | 3.40 | 8.90 | 2.63 | 1.10 | 1.01 | 73.60 | 23.21 | 50.39 | 68.82 |
| Mg4Al1 + 0.25% Cu | N2 | 2.69 | 0.56 | 2.77 | 6.00 | 32.83 | 0.22 | 54.55 | 6.14 | 48.29 | 40.66 |
| Mg4Al1 + 0.25% Cu | H2 | 7.63 | 19.79 | 14.71 | 4.69 | 1.24 | 5.05 | 46.89 | 14.92 | 31.97 | 65.93 |

The ratio between Mg and Al in the LDH has an impact on selectivity and conversion of the product. Characterization of the catalyst by XAS reveals that different Mg/Al ratios in the support can change the mobility of copper atoms during the reaction conditions. It is clear that the copper is much more easily reduced to its metallic state, even doing so without the presence of ethanol. Under ethanol flow, copper is almost entirely reduced to $Cu^0$, with Cu—Cu bonding in the EXAFS data signifying the aggregation of copper clusters. The $Mg_4Al_1$+0.1% Cu catalyst shows no trace of metallic copper under the same conditions, despite the same metal loading and synthesis procedure. In Table 3, the product selectivities obtained from different Mg/Al ratio catalyst are compared. It can be seen that a Mg/Al ratio of 4 represents the optimal results in regards to higher alcohols thus much more resistant to sintering, provided that the concentration of copper is sufficiently low. Minimizing the side reaction pathways as the product spectrum seems to be dictated primarily by the species of copper rather than the absolute concentration.

This divergent response to the synthesis method at lower Cu concentrations is reflected in the XAS data as well. Comparing the XANES data between the coprecipitated and impregnated 0.25% Cu catalysts there seems to be little difference between the two different spectra, with almost all of the copper present as the $Cu^0$ species. At the 0.1% Cu concentration however, the obtained spectra differ greatly between the synthesis methods. Coprecipitation only produces $Cu^{+1}$ species during the reaction, while the impregnated catalyst has a clear mix of the $Cu^{+1}$ and $Cu^0$ species.

TABLE 4

| | Aldehydes | Ketones | Esters | Alkenes | Ethers | CO2 | Total Alcohols | Higher Alcohols | 1-Butanol | Conversion |
|---|---|---|---|---|---|---|---|---|---|---|
| Mg4Al1 + 0.1%Cu Coprecipitated | 9.36 | 3.40 | 8.90 | 2.63 | 1.10 | 1.01 | 73.60 | 23.21 | 50.39 | 68.82 |
| Mg4Al1 + 0.1%Cu Impregnated | 9.44 | 8.61 | 22.12 | 4.41 | 3.42 | 2.08 | 49.62 | 12.12 | 37.51 | 55.30 |
| Mg4Al1 + 0.25%Cu Coprecipitated | 7.63 | 19.79 | 14.71 | 4.69 | 1.24 | 5.05 | 46.89 | 14.92 | 31.97 | 65.93 |
| Mg4Al1 + 0.25%Cu Impregnated | 8.69 | 15.92 | 22.28 | 3.39 | 0.46 | 3.25 | 46.01 | 12.57 | 33.44 | 56.67 |

TABLE 5

Ethanol conversion and product distribution for varying copper loadings

| Cu Loading [mol %] | Conv. [mol %] | Carbon Selectivity [mol %] | | | | | | | | | | |
|---|---|---|---|---|---|---|---|---|---|---|---|---|
| | | Ethers[a] | EY[b] | Acet[c] | BuOH[d] | Butenol[e] | $C_{6+}$OH[f] | Diene[g] | Butenes[h] | EtAc[i] | $C_{6+}$Ester[j] | Ketone[k] |
| 0 | 33.88 | 46.09 | 2.04 | 0.51 | 35.06 | 0.27 | 4.80 | 1.04 | 8.26 | 0.59 | 0.04 | 0.20 |
| 0.025 | 37.99 | 3.82 | 0.29 | 4.59 | 61.25 | 0.20 | 16.51 | 0.00 | 5.27 | 2.63 | 2.75 | 1.30 |
| 0.05 | 46.93 | 2.49 | 0.00 | 3.28 | 62.46 | 0.00 | 19.69 | 0.00 | 0.84 | 1.82 | 4.10 | 2.32 |
| 0.1 | 59.32 | 2.10 | 0.00 | 5.06 | 56.29 | 0.00 | 26.52 | 0.00 | 1.16 | 1.42 | 3.05 | 3.18 |
| 0.25 | 69.62 | 2.82 | 0.00 | 5.09 | 29.60 | 0.00 | 18.34 | 0.00 | 0.27 | 1.96 | 4.20 | 24.85 |

Reactions Conditions.
[a]Ethers.
[b]Ethylene.
[c]Acetaldehyde.
[d]1-Butanol.
[e]2-Buten-1-ol.
[f]1-Hexanol, 2-ethyl-1-butanol, 1-octanol, 2-ethyl-1-hexanol.
[g]1,3-Butadiene.
[h]1-Butene, 2-butene.
[i]Ethyl Acetate.
[j]Ethyl butyrate, butyl acetate, butyl butyrate.
[k]Acetone, 2-Pentanone, 4-heptanone, 2-Heptanone The catalysts were compared using the ethanol coupling reaction in a pressurized packed bed flow reactor, under $H_2$ flow at 325° C. The ethanol conversion and carbon selectivity of the products were analyzed after 60 hours on stream to compare the reactions at steady state conditions. The results are shown below in Table 5. The support LDH shows 40% selectivity to conversion of ethanol to higher alcohols owing to the presence of mixed acid and base sites. The high amounts of ethers and hydrocarbons formed over LDH structure is due to the prevalence of acid site catalyzed dehydration, signifying that the dehydrogenation of ethanol is not highly competitive with its dehydration to diethyl ether.

Post synthesis calcination affects both the final stability of the copper as well as the surface acid-base sites of the support. If the calcination temperature is not sufficiently high, the conversion is low and all the synthesis salts may not be burned away. At higher calcination temperatures, the emergence of a strong MgO phase as well as the presence of spinel phases at 1000 C help lock the copper in place, preventing the copper from aggregating and reducing the ketones and esters formed, while promoting both higher conversion as well as higher alcohol production. However, the catalyst also generates much more hydrocarbon products resulting from dehydration, and the catalyst is prone to rapid deactivation. At 600 C, the catalyst has more long term stability along with high conversion, making it suitable for practical use.

TABLE 6

| | Aldehydes | Ketones | Esters | Alkenes | Ethers | CO2 | Total Alcohols | Higher Alcohols | 1-Butanol | Conversion |
|---|---|---|---|---|---|---|---|---|---|---|
| 400 C. | 9.33 | 2.34 | 8.49 | 6.11 | 1.80 | 0.86 | 71.06 | 17.73 | 53.32 | 50.23 |
| 600 C. | 9.36 | 3.40 | 8.90 | 2.63 | 1.10 | 1.01 | 73.36 | 23.21 | 50.39 | 68.82 |
| 800 C. | 9.50 | 2.05 | 6.48 | 3.64 | 1.64 | 0.66 | 75.99 | 27.98 | 47.99 | 75.77 |
| 1000 C. | 9.29 | 1.41 | 4.63 | 5.06 | 1.99 | 0.47 | 77.00 | 29.23 | 47.65 | 72.43 |

The addition of copper to these sites results in passivation of the strongly basic sites and weak acidic sites and promotes the strength and number of weakly basic sites that are useful for the condensation reaction. Increasing copper concentration is correlated with a continuous rise in ethanol conversion suggesting that the copper increases the conversion of ethanol by promoting the initial dehydrogenation of ethanol which is considered to be the rate determining step over the LDH derived mixed oxide materials. Two significant changes in the product profile were observed at the initial introduction of copper on the support and at copper concentrations above 0.1%. Regarding the first, the addition of copper dramatically promotes the formation of higher alcohols over ethers and dehydrated product compared to the LDH support, improving selectivity to alcohols from 41% to 80.7%. The ethers and hydrocarbons result from the acid site-catalysed dehydration of ethanol, a competitive reaction to the dehydrogenation of ethanol that leads to all other observed products.

This suggests that the copper lowers the energy barrier for dehydrogenation of ethanol compared to the dehydration, and is further supported by the return of these same dehydration products during deactivation of the catalyst. Minimal copper loading was shown to be capable of promoting the dehydrogenation of ethanol over dehydration. However, its presence also led to the formation of ketones and esters which were not observed on the unpromoted catalyst, and are formed subsequent to ethanol dehydrogenation.

Adding copper up to 0.1% loading had limited effect on these side products; as a result, the high selectivity to alcohols was maintained even as conversion jumped from 37% to 59% at the 0.1% Cu loading. Higher conversion at similar selectivity suggests that the additional copper atoms promote the chemical conversion of ethanol to products through the same pathway, with none of the intermediate steps being rate limited. It also suggests that these additional copper atoms are chemically equivalent and do not significantly change the acid base properties of the LDH support at concentrations less than or equal to 0.1% A copper loading. Increasing to 0.25% Cu caused another significant shift in the product distribution, with selectivity towards ketones rising to 24.9% with a corresponding drop in the overall selectivity to alcohols to 49%. As a result, the overall yield to higher alcohols decreased in comparison with the 0.1% Cu catalyst, despite an improved ethanol conversion of 69.6%. It appears that beyond 0.1% copper addition, two chemically dissimilar copper sites are formed on the LDH derived mixed oxide support that promotes two different reaction pathways for ethanol conversion.

The increase in ethanol conversion appears to correlate with the availability of the copper on the surface increasing the dehydrogenation of ethanol, a preliminary step to the formation of all the products and that copper may still be atomically dispersed on the LDH support. This is a distinct region of copper concentration where the metal directly participates in the ethanol conversion without significantly affecting the formation of side products. At copper concentrations higher than 0.25%, the production of ketones become the predominant chemical pathway and higher alcohols become a minor product.

To demonstrate the stability of the low copper catalysts, we performed an extended run of the ethanol coupling reaction over the 0.1% Cu catalyst. The catalyst proved capable of maintaining high catalytic activity for over 600 hours of time on stream, with less than 10% drop in conversion and selectivity over the run. The experiment was scheduled to stop at 600 hours and not stopped due to the deactivation. Deactivation of the catalyst occurred slowly over time, marked primarily by the rise in dehydration products such as diethyl ether and 1-butene. The stability of the catalyst indicates that the copper in the catalyst is resistant to the sintering that would normally be expected at these temperatures, resulting in undiminished dehydrogenation activity. The lack of change in the ketone products also implies that there is no significant changes in the type of copper active site on the catalyst surface.

Figure 2A:
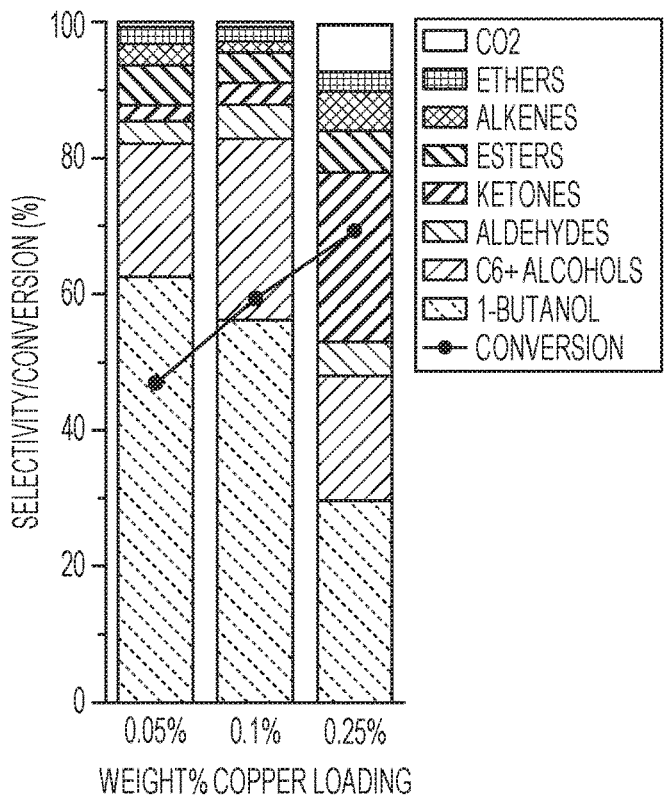
FIG. 2(a) shows the carbon selectivity and conversion of ethanol coupling reaction for different copper concentrations after 60 hours on stream shows high selectivity to higher alcohols at copper loadings at 0.1 wt % and below, while the conversion of ethanol increases with increase in total copper concentration.
Figure 2B:
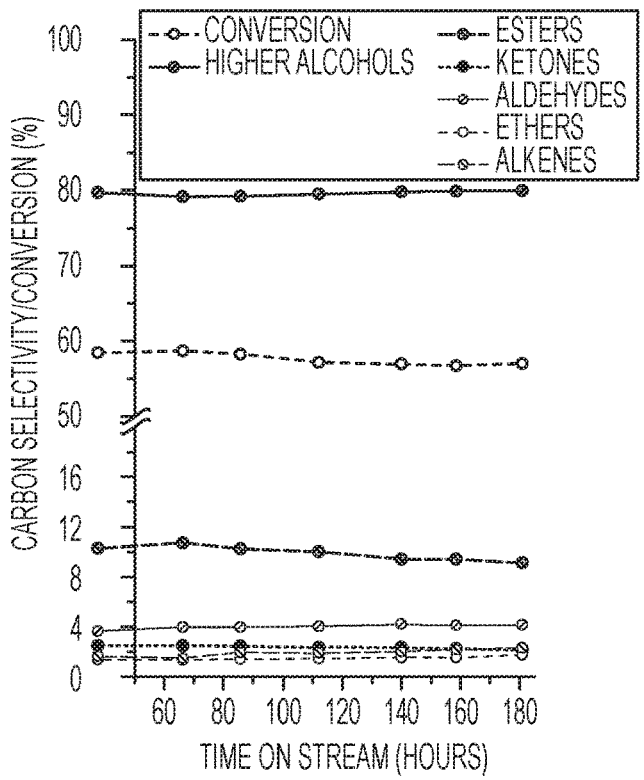
FIG. 2(b) shows results for an extended lifetime test of 0.1% Cu catalyst show that the selectivity of more than 75% can be achieved for nearly 200 hours of continuous operation of the catalyst, indicating stability in the copper active sites
Figure 3A:
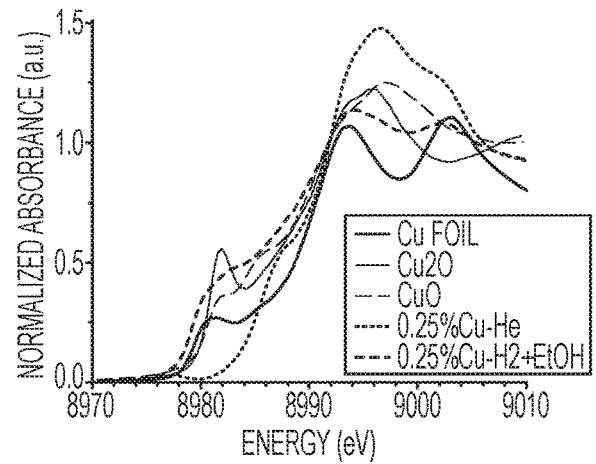
FIG. 3(a)-(d) show in operando XANES and EXAFS spectra demonstrating difference in copper speciation between 0.25% Cu and 0.1% Cu catalysts. Normalised XANES spectra of Cu K-Edge in operando for (a) 0.1% Cu and (b) 0.25% Cu catalysts. Fourier transform EXAFS spectra for (c) 0.1% Cu and (d) 0.25% Cu.
Figure 3B:
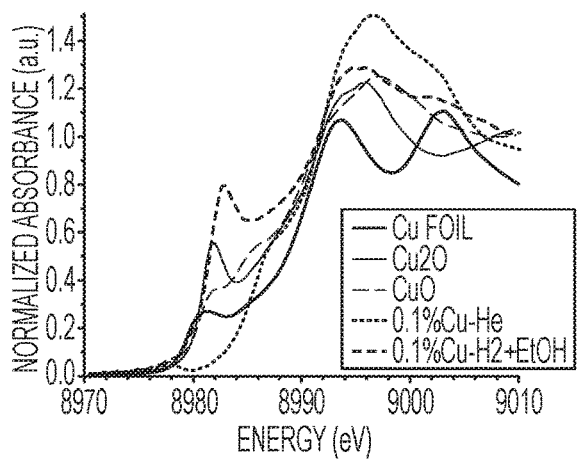
Figure 3C:
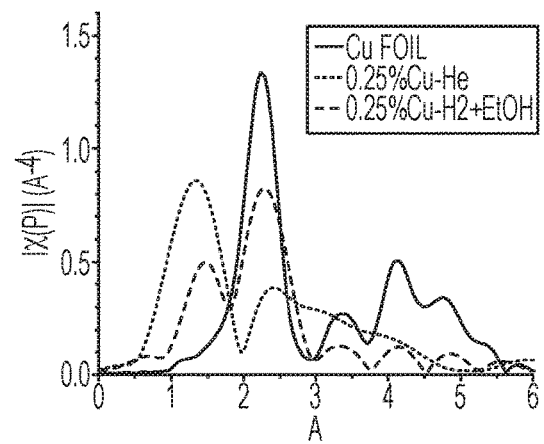
Figure 3D:
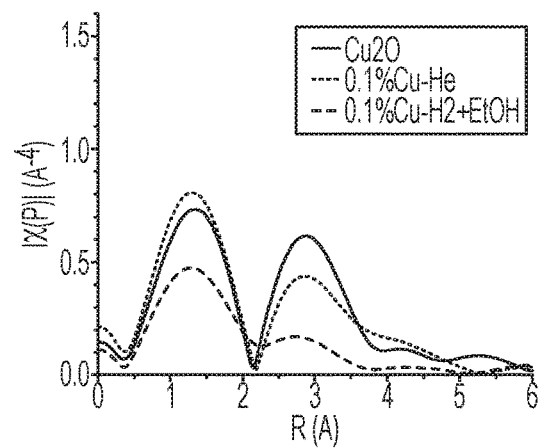

Direct evidence for the high dispersion of copper was obtained from HAADF imaging and EDS mapping analysis, as presented in FIG. 2 for the 0.25 wt % and 0.1 wt % Cu catalysts. The HAADF imaging suggests that the spent the 0.1 wt % Cu catalyst maintains a high dispersion of Cu across the surface of LDH as no catalytic clusters and nanoparticles could be identified. It must be noted that imaging of individual copper atoms on LDH support is difficult due to a small difference in their atomic numbers resulting in poor imaging contrast. On the other hand, the results for 0.25 wt % Cu catalyst reveal numerous nanoparticles of copper with sizes >5 nm. It is thus suggested that for copper concentrations equal to or lower than 0.1 wt %, Cu is resistant to sintering, and thus maintain high dispersion, while for higher concentrations such as 0.25% the copper species are mobile resulting in their sintering and agglomeration to >5 nm nanoparticles.

Measurements of the spent catalysts showed significant differences however; the 0.1 wt % Cu catalyst maintained its uniform dispersion, while the results for the 0.25 wt % Cu catalyst reveal numerous clusters of copper with sizes >5 nm. Addition of copper at concentrations equal to or lower than 0.1 wt % results in formation of sinter resistant dispersion of copper; however at concentrations greater than 0.1% the copper species are mobile resulting in their sintering and agglomeration to 5 nm clusters. To verify the dispersion at the monoatomic level, extended x-ray absorbance fine structures (EXAFS) spectra were analyzed for evidence of Cu—Cu bonding.

Calcined catalysts were prepared at copper weight concentrations of 0.1%, 0.25%, 0.5%, and 6% copper and run together in operando, by first reducing at 325° C. under flowing $H_2$ until changes in the XANES spectra were stabilized, and then followed by bubbling ethanol with the $H_2$ gas to begin. Though not detected in the calcined samples, the peak at 2.55 Å corresponding to Cu—Cu bonding quickly appeared upon reduction, and became the predominant peak by the end of the reaction. The 0.1% Cu catalyst was the only one to show no signs of Cu—Cu contributions, exhibiting the same peaks before and after reduction. These results confirm the observations from TEM, demonstrating that copper can be monoatomically dispersed in co-precipitated LDH derived catalyst, but the dispersion typically needs to be stably maintained under reductive conditions at concentrations above 0.1% Cu.

A combination of the Cu K-Edge XANES and EXAFS was used to elucidate the nature and structure of the copper active site. XANES spectra for the calcined catalysts were similar, all exhibiting the intense white line characteristic of $Cu^{2+}$. The weak pre-edge feature at ~8979 eV, assigned to the dipole forbidden and quadrupole allowed 1s→3d transition, indicates the incorporation of copper in a slightly distorted octahedral coordination. The shoulder feature at ~8987 eV is attributed to the 1s→4s transition, resulting Jahn-Teller distortion. The features can be considered typical for $Cu^{+2}$ in a six coordinated environment. EXAFS confirmed formation of fitting was performed using the periclase (MgO), substituted with a copper atom at the center.

Reduction of the catalysts using $H_2$ gas resulted in different changes in copper speciation depending on the concentration. At the highest loading, the 6% Cu was immediately reduced to the $Cu^0$ state, characterized by the loss of the white line and pre-edge features of $Cu^{+2}$ and the appearance of a strong shoulder at 8980 eV. The spectra remained unchanged over time, indicating the reduction was immediate and complete. At lower concentrations, the copper was shown to reduce first to $Cu^{+1}$ state, characterized by the decrease in intensity of the white line at 8996 eV, and a sharp peak at the ~8983 eV. This feature, though shifted by ~2 eV compared to the peak seen $Cu_2O$, is typical for supported copper materials, where monovalent copper is often seen a transitionary species during reduction. This is most apparent for the 0.25% Cu catalyst, where it can be seen that a $H_2$ environment is not sufficient to fully reduce copper to its metallic state. The addition of ethanol in operando appears to be what allows for the rapid reduction from $Cu^{+1}$ to $Cu^0$.

XANES spectra for the 0.1% Cu catalyst showed that the combination of $H_2$ and ethanol were only sufficient to produce the $Cu^{+1}$ species. The absence of any features below 8983 eV denote the absence of $Cu^0$, indicating that the reported catalytic activity for the 0.1% Cu can solely attributed to monovalent copper. Though reports of mixed $Cu^{+1}$/$Cu^0$ have report This $Cu^{+1}$ oxidation state, typically observed as a transition or intermediate state, was found be stable in operando for over 5 hours, with a total of 12 hours under reductive atmosphere at 325° C. Similarly, the $Cu^{+1}$ state was also found to be stabilized when re-exposed to atmosphere. The spent 0.25 wt % Cu catalyst recovered after in operando experiments was left in air for 24 hour before reanalysis with XANES revealed a still prominent peak at 8983 eV, marking the slow reversion of $Cu^{+1}$ to $Cu^{+2}$. This stability suggests a strong interaction between the metal and support, preventing the high mobility of single atoms characteristic for copper.

This is further clarified by the EXAFS, where the $Cu^{+2}$ to $Cu^{+1}$ is marked by two major trends: (1) the bond length of Cu—O first shell is shorted from 1.98 A to 1.86 Å(2) the reduction in amplitude of the Cu—Mg second shell. Comparing the FT-EXAFS for the 0.1% Cu at steady state in operando against the fresh catalyst shows the amplitude loss of the first shell, correlating with a drop in coordination number. At the same time, the Cu—O peak shifts left, signifying the shortening of the bond length. The amplitude of the Cu—Mg shell shows a sharper drop, corresponding to a decrease in coordination number. This suggests movement of the copper atoms from place deeper in the support lattice to a more exposed location, likely closer to the surface. The aforementioned absence of the Cu—Cu peak as well as the lack of any signs of $Cu^0$ in the XANES suggest that the $Cu^{+1}$ oxidation state is dependent on copper being supported on isolated sites. Examination of the EXAFS spectra for 0.25% Cu shows how the loss of the Cu—Mg shell quickly results in the formation of Cu—Cu bonds, indicating the formation of the nanoclusters observed under TEM. The retention of the Cu—O—Mg bond is thus a factor in stabilizing the monovalent copper species.

TABLE 6

| Fitting EXAFS spectra of catalysts ex-situ and in operando | | | | | |
|---|---|---|---|---|---|
| Sample | Shell$^a$ | CN$^b$ | r (Å)$^c$ | DW$^d$ | E$t^f$ |
| 0.25%C Ex-Situ | Cu—O | 4.37 | 1.84 | .016 | 5.175 |
|  | Cu—O (2) | 5.12 | 2.71 | .031 | 5.175 |
|  | Cu—Mg | 20.12 | 2.99 | .013 | 5.175 |
| 0.25%Cu In Operando | Cu—O | 1.62 | 1.84 | .019 | 1.568 |
|  | Cu—Cu | 12.85 | 2.55 | .023 | 1.568 |
|  | Cu—O | 0.706 | 1.74 | .017 | 0.18 |

TABLE 6-continued

| Fitting EXAFS spectra of catalysts ex-situ and in operando | | | | | |
|---|---|---|---|---|---|
| Sample | Shell$^a$ | CN$^b$ | r (Å)$^c$ | DW$^d$ | E$t^f$ |
| 0.1%C Ex-Situ | Cu—O (2) | 0.15 | 1.90 | .036 | 0.18 |
|  | Cu—Mg | 11.07 | 2.95 | .029 | 0.18 |
| 0.1%Cu In Operando | Cu—O | 0.78 | 1.70 | .003 | 0.838 |
|  | Cu—O (2) | 0.05 | 1.86 | .018 | 0.838 |

Comparison of the XAS data with the results from the catalytic reaction clearly associates the change in product selectivity above 0.1% Cu with the loss of the single atom monovalent copper sites and the introduction of metallic copper. The rise in ketone products can be understood as a result of the C—C scission and decarbonylation of the coupled intermediate, a reaction has been reported previously for copper surfaces. Our results show that even low concentrations of metallic copper are active in promoting this pathway.

Figure 4:
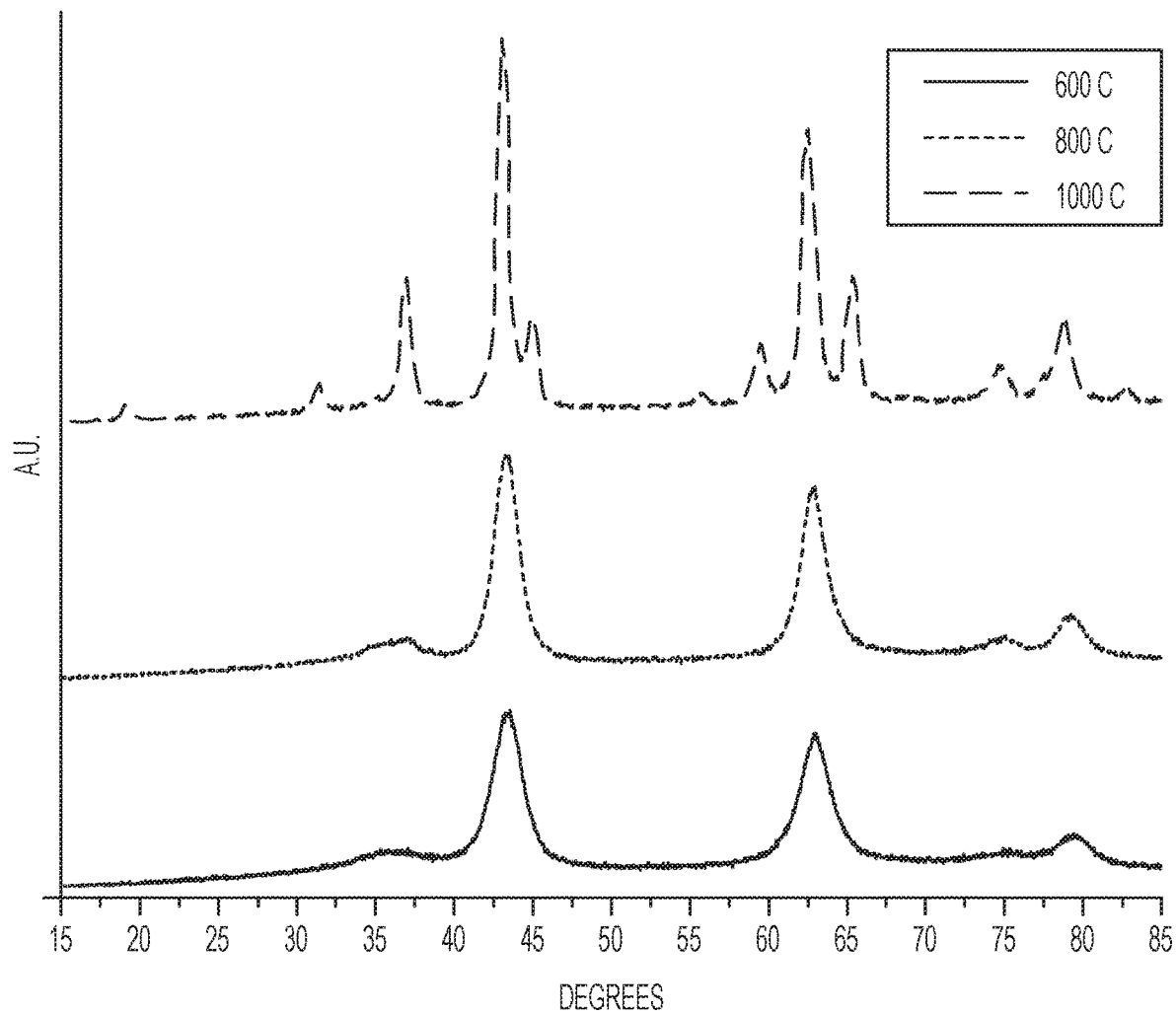
FIG. 4 shows XRD results for samples at increasing calcination temperatures show the change in the hydrotalcite phase and structure.

For example FIG. 4 shows that at 600 C, only an amorphous MgO XRD spectra is visible, with substantial peak broadening. At 800 C, the MgO phase becomes more prevalent with less peak broadening suggesting a stronger phase formation. At 1000 C, additional peaks representing the newly formed spinel MgAl2O¬x phase appear, as well as a continued sharpening of the MgO peaks. The increasing crystallinity and separation of phases suggest that the copper atoms in the solid solution become more tightly bound to the support with a significant reduction to the mobility of copper under the reductive reactions conditions. This is reflected in the reduced ester and ketone selectivity as calcination temperature increases.

However, our research has shown that the presence of these sites on a stabilized stable copper pseudo-single-atom supported on $MgO$—$Al_2O_3$ catalyst serves as a highly selective and effective catalyst with superior performance in alcohol coupling. For the first time ethanol condensation to higher alcohols at ~50% yields and ~80% selectivity is demonstrated with stable catalyst lifetime over 500 hours in a continuous flow system. These catalytic transformations of alcohols can provide a direct path towards the sustainable production of numerous commodity chemicals from renewable sources, replacing traditional petrochemical processes.

The high $H_2$ partial pressures in the system can be further leveraged in the design of such a reactor setup that allows for process intensification via in-line hydrogenation beds to further raise the selectivity to alcohol products. The hydrogenation of aldehydes is an example of such a process that can be performed directly after the primary Guerbet reaction bed under the same pressure without separation. Those skilled in the art will understand this chemistry is easily achievable under such $H_2$ partial pressures using a wide range of commonly known heterogeneous catalysts with metal promoters, which can include but are not limited to copper, platinum, palladium, rhenium, rhodium, ruthenium, nickel, cobalt, etc. The reaction over this second bed will can be thus optimized under the selection of an appropriate catalyst and temperature regime for the hydrogenation reaction to unwanted hydrogenation of products while maximizing yield. The high $H_2$ partial pressure allows such a reaction to proceed at milder temperatures and greater weight hourly space velocity (WHSV).

As an example, Table 7 shows the results obtained from such a double bed reactor system, with the first bed filled of $Mg_4Al_1+0.1\%$ Cu under 300 psig $H_2$ and 325° C. and the second bed of copper chromite at 180° C. loaded in the same reactor directly after the first bed, with all other conditions and analysis as described previously. The most significant effect of the addition of the hydrogenation bed is the effective elimination of aldehydes via conversion to their corresponding alcohols, resulting in greater selectivities to 1-butanol as well as higher alcohols. Low concentrations of ketones present in the product mixture will also be largely hydrogenated to their respective alcohols, increasing the total selectivity to alcohols to above 80%. The hydrogenation of acetaldehyde to ethanol accounting for the slight drop in conversion. In addition to the improved higher alcohol selectivity, the addition of hydrogenation bed reduces the number of different compounds in the product mixture thus simplifying the downstream product purification and ethanol feed recycle.

The high $H_2$ partial pressure of the system can allow for further increase in product selectivity via the hydrogenolysis of esters to their respective constituent alcohols in an in-line reaction bed without product separation. The ester hydrogenolysis reaction requires higher $H_2$ pressures and would typically require an entirely separate reactor system. Our Guerbet catalyst remains effective at $H_2$ partial pressure ranges up to 750 pisg, providing a large window for the effective hydrogenolysis of esters whose effectiveness benefits greatly from increased $H_2$ partial pressures. This allows for the potential elimination of a major impurity group from the Guerbet product stream. Furthermore, the majority of the ester products present at optimal Guerbet reaction conditions are $C_{6+}$ in size, such that the nearly all the products from hydrogenolysis of these esters would be the desired higher alcohol. Those skilled in the art will understand that ester hydrogenolysis can be achieved using a number of catalysts, which can include but are not limited to carbon or mixed oxide supports promoted by some combination of metals such as ruthenium, copper, chromium, palladium, rhenium, iridium, etc. The catalyst and reaction temperature can be chosen to optimize for higher alcohols products while minimizing over hydrogenated products. Those skilled in the art will also understand that conditions necessary for ester hydrogenolysis will also be adequate for the hydrogenation of aldehydes, and that the catalysts chosen for hydrogenolysis will similarly be appropriate. Thus, a double bed system can be achieved where the two largest impurities in the original products stream, esters and aldehydes, can be converted to alcohol products in one step. As an example, the results of ester hydrogenolysis of product from the primary Guerbet reaction is shown in Table 7.

TABLE 7

|  | Aldehydes | Ketones | Esters | Alkenes | Ethers | CO2 | Total Alcohols | Higher Alcohols | 1-Butanol | Conversion |
|---|---|---|---|---|---|---|---|---|---|---|
| Guerbet | 9.36 | 3.40 | 8.90 | 2.63 | 1.10 | 1.01 | 73.60 | 23.21 | 50.39 | 68.82 |
| Guerbet w/ Hydrogenation | 0.68 | 1.22 | 11.12 | 2.02 | 1.90 | 0.97 | 83.06 | 28.63 | 54.43 | 62.09 |

The present disclosure provides examples of catalysts and process for converting ethanol and ethanol containing feedstocks to higher alcohols using Guerbet condensation chemistry at a high selectivity. This provides a high number of advantages over the prior art including the ability to perform this conversion of ethanol to a higher alcohol in one catalytics bed, the selectivity to higher alcohol is about 90 percent which is very high compared to other known technology, demonstrated the catalyst lifetime to be around 250 hours without any deactivation towards selectivity of the conversion and the catalyst is made up of low cost CuO—MgO—Al2O3 via simple co-precipitation procedure. This provides a significant advance in enabling the greater implementation and adoption of renewable resources such as ethanol in the future.

Additional objects, advantages and novel features of the present invention are described herein and will become further readily apparent to those skilled in this art from the following detailed description. In the preceding and following descriptions this work has shown and described only the preferred embodiment of the invention, by way of illustration of the best mode contemplated for carrying out the invention. As will be realized, the invention is capable of modification in various respects without departing from the invention. Accordingly, the drawings and description of the preferred embodiment set forth herein are to be regarded as illustrative in nature, and not as restrictive.

What is claimed is:

1. A method for converting an alcohol containing feedstock containing ethanol, the method comprising the steps of:
   introducing the feedstock to a co-precipitated CuO—MgO—$Al_2O_3$ catalyst having dispersed and stabilized Cu 1+ copper sites at an atomic level (pseudo-single atom) on a MgO—$Al_2O_3$ catalyst, wherein the copper percentage is between 0.025 wt % and 0.25 wt % under a hydrogen carrier gas at a pressure above 100 psig and at a temperature between 275-350 degrees C. to facilitate in-line process intensification selectively form a preselected higher alcohol product.

2. The method of claim 1 wherein the catalyst is a sinter resistant catalyst.

3. The method of claim 1 further comprising the step of condensing the preselected higher alcohol product through a Guerbet reaction to yield a second product.

4. The method of claim 3 further comprising the step of: passing the second product from the Guerbet reaction through a second catalyst bed to improve selectivity to alcohols via conversion of esters and aldehydes and minimize downstream separation.

* * * * *